(12) United States Patent
Lux et al.

(10) Patent No.: US 9,870,457 B2
(45) Date of Patent: Jan. 16, 2018

(54) HERMA—HEARTBEAT MICROWAVE AUTHENTICATION

(71) Applicant: California Institute of Technology, Pasadena, CA (US)

(72) Inventors: James Paul Lux, Thousand Oaks, CA (US); Edward Chow, Walnut, CA (US); Michael Ray McKee, Lancaster, CA (US); Salman-ul Mohammed Haque, Los Angeles, CA (US); Andre Tkacenko, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/828,452

(22) Filed: Aug. 17, 2015

(65) Prior Publication Data
US 2016/0048672 A1    Feb. 18, 2016

Related U.S. Application Data

(60) Provisional application No. 62/038,128, filed on Aug. 15, 2014.

(51) Int. Cl.
*G06F 21/32* (2013.01)
*A61B 5/05* (2006.01)
(Continued)

(52) U.S. Cl.
CPC .......... *G06F 21/32* (2013.01); *A61B 5/02444* (2013.01); *A61B 5/0507* (2013.01);
(Continued)

(58) Field of Classification Search
CPC .. G06F 21/32; G06F 21/83; G06F 2221/2139; G06F 3/017; G06F 19/3462;
(Continued)

(56) References Cited

U.S. PATENT DOCUMENTS

| 4,641,349 A | 2/1987 | Flom et al. |
| 5,486,833 A | 1/1996 | Barrett |

(Continued)

FOREIGN PATENT DOCUMENTS

WO    2016025961 A1    2/2016

OTHER PUBLICATIONS

International Search Report and Written Opinion for International Application No. PCT/US2015/045577, Search completed Oct. 13, 2015, Mailed Nov. 12, 2015, 11 Pgs.

(Continued)

*Primary Examiner* — Mark Blouin

(74) *Attorney, Agent, or Firm* — KPPB LLP

(57) ABSTRACT

Systems and methods for identifying and/or authenticating individuals utilizing microwave sensing modules are disclosed. A HEaRtbeat Microwave Authentication (HERMA) system can enable the active identification and/or authentication of a user by analyzing reflected RF signals that contain a person's unique characteristics related to their heartbeats. An illumination signal is transmitted towards a person where a reflected signal captures the motion of the skin and tissue (i.e. displacement) due to the person's heartbeats. The HERMA system can utilize existing transmitters in a mobile device (e.g. Wi-Fi, Bluetooth, Cellphone signals) as the illumination source with at least one external receive antenna. The received reflected signals can be preprocessed and analyzed to identify and/or authenticate a user.

24 Claims, 9 Drawing Sheets

(51) Int. Cl.
H04W 12/06 (2009.01)
H04L 29/06 (2006.01)
A61B 5/024 (2006.01)
(52) U.S. Cl.
CPC ......... *H04L 63/0861* (2013.01); *H04W 12/06* (2013.01); *A61B 5/02438* (2013.01)
(58) Field of Classification Search
CPC .......... G06F 21/31; G06F 21/34; G06F 21/35; G06F 21/36
USPC ...................................................... 340/5.82
See application file for complete search history.

(56) References Cited

U.S. PATENT DOCUMENTS

| | | | |
|---|---|---|---|
| 5,774,571 | A | 6/1998 | Marshall |
| 5,913,196 | A | 6/1999 | Talmor et al. |
| 6,125,192 | A | 9/2000 | Bjorn et al. |
| 6,554,705 | B1 | 4/2003 | Cumbers et al. |
| 6,606,511 | B1 | 8/2003 | Ali |
| 7,206,938 | B2 | 4/2007 | Bender et al. |
| 7,272,431 | B2 | 9/2007 | McGrath et al. |
| 7,417,536 | B2 * | 8/2008 | Lakshmanan ....... B60R 21/0132 340/438 |
| 7,811,234 | B2 | 10/2010 | McGrath et al. |
| 7,889,053 | B2 | 2/2011 | McGrath et al. |
| 8,232,866 | B2 * | 7/2012 | McGrath ............ G07C 9/00158 340/5.1 |
| 8,884,809 | B2 * | 11/2014 | Hyde ...................... G01S 13/86 340/573.1 |
| 9,151,834 | B2 * | 10/2015 | Hyde ...................... G01S 7/412 |
| 2002/0002335 | A1 | 1/2002 | Doten |
| 2002/0138768 | A1 | 9/2002 | Murakami |
| 2004/0017300 | A1 | 1/2004 | Kotzin |
| 2004/0086091 | A1 | 5/2004 | Naidoo |
| 2005/0220310 | A1 | 10/2005 | McGrath et al. |
| 2007/0257787 | A1 | 11/2007 | McGrath et al. |
| 2008/0045832 | A1 | 2/2008 | McGrath et al. |
| 2009/0067286 | A1 | 3/2009 | Bose et al. |
| 2010/0008449 | A1 | 1/2010 | Sayers et al. |
| 2010/0194571 | A1 | 8/2010 | Ortiz |
| 2011/0066041 | A1 | 3/2011 | Pandia |
| 2012/0068819 | A1 | 3/2012 | McGrath et al. |
| 2012/0269102 | A1 | 10/2012 | Nicholls et al. |
| 2013/0005310 | A1 | 1/2013 | Lim |
| 2014/0163362 | A1 | 6/2014 | Pahlevan et al. |

OTHER PUBLICATIONS

International Preliminary Report on Patentability for International Application PCT/US2015/045577, Report dated Feb. 21, 2017, dated Mar. 2, 2017, 10 Pgs.
Biel et al., "ECG analysis: A new approach in human identification", IEEE Transactions Instrumentation and Measurement, vol. 50, No. 3, Jun. 2001, pp. 808-812.
Chan et al., "Wavelet Distance Measure for Person Identification Using Electrocardiograms", IEEE Transactions Instrumentation and Measurement, vol. 57, No. 2, Feb. 2008, pp. 248-253.
Chow et al., "Autonomous Information Unit (AIU) for Fine-Grain Data Access Control and Mission Data Protection in Net-Centric System Testing Environment", JPL New Technology Report #48224, 2012, 2 pages.
Chow, "Autonomous Information Unit: Why Making Data Smart Can Also Make Data Secured?", 15th IEEE International Workshops on Enabling Technologies: Infrastructure for Collaborative Enterprises, WETICE '06, 2006, 6 pages.
Feng et al., "Continuous Mobile Authentication using Touchscreen Gestures", 12th IEEE Conference on Technologies for Homeland Security, Nov. 13-15, 2012, pp. 451-456.
Israel et al., "ECG to identify individuals", Pattern Recognition, vol. 38, No. 1, 2005, pp. 133-142.
Kyoso et al., "Development of an ECG identification system", Proc. 23rd IEEE Engineering in Medicine and Biology Conference, 2001, vol. 4, pp. 3721-3723.
Lin et al., "Biometric verification using thermal images of palm-dorsa vein patterns", IEEE Transactions on Circuits and Systems for Video Technology, vol. 14, Issue 2, Feb. 2004, pp. 199-213.
Tawfik et al., "Human Identification Using QT Signal and QRS Complex of the ECG", The Online Journal on Electronics and Electrical Engineering, vol. 3, No. 1, 2010, pp. 383-387.
Wang et al., "Integrating Analytic and Appearance Attributes for Human Identification from ECG Signals", 2006 Biometrics Symposium: Special Session on Research at the Biometric Consortium Conference, Aug. 21-Sep. 19, 2006, pp. 1-6.
Yang et al., "Biometric Recognition Using Three-Dimensional Ear Shape", University of Notre Dame Report # TR-2006-01, 2006, 30 pages.
"Arduino HomePage", Arduino, Feb. 1, 2014, https://web.archive.org/web/20140201142732/https://www.arduino.cc/, 3 pages.
"Autoregressive model", Wikipedia, Dec. 8, 2013, retrieved from https://web.archive.org/web/20150106061833/https://en.wikipedia.org/wiki/Autoregressive_model on Jul. 26, 2017, 9 pages.
"EMMDAR (Electro-Magnetic Motion Detection and Ranging)", L3 Communications CyTerra, retrieved from http://www.cyterra.com/products/emmdar.htm on May 23, 2017, 1 page.
"fieldnames", MathWorks, Nov. 28, 2013, https://web.archive.org/web/20131128081202/http://www.mathworks.com/help/matlab/ref/fieldnames.html, 2 pages.
"Least squares", Wikipedia, Jan. 30, 2014, https://web.archive.org/web/20140209133957/https://en.wikipedia.org/wiki/Least_squares on Jul. 26, 2017, 9 pages.
"str2num", MathWorks, Jul. 17, 2013, retrieved from https://web.archive.org/web/20130717105438/http://www.mathworks.com/help/matlab/ref/str2num.html, 2 pages.
"SuperVision 1600 Handheld ThroughWall Radar Delivers Unique 2D View That Can Revolutionise Security Work", Yiwu Tianying Optical Instrument Co., Limited, May 11, 2010, retrieved from https://web.archive.org/web/20100511054443/http://www.nightvisioncn.com/sdp/625512/4/cp-5246844/0/Through_Wall_Rada.html on May 23, 2017, 3 pages.
"Teensy USB Development Board", PJRC Store, Feb. 9, 2014, retrieved from https://web.archive.org/web/20140209222648/www.pjrc.com/store/teensy3.html, 1 page.
"Teensyduino", PJRC, Feb. 9, 2014, https://web.archive.org/web/20140209215538/https://www.pjrc.com/teensy/teensyduino.html, 3 pages.
"textscan", MathWorks, Dec. 19, 2013, retrieved from https://web.archive.org/web/20131219081941/http://www.mathworks.com/help/matlab/ref/textscan.html, 3 pages.
"TiaLinx, Inc. Company", TiaLinx, Inc., retrieved from http://www.tialinx.com/company.html on May 23, 2017, 3 pages.
"Troubleshooting Common Problems", PJRC, Feb. 9, 2014, https://web.archive.org/web/20140209214600/https://www.pjrc.com/teensy/troubleshoot.html, 5 pages.
"Xaver Products", Camero, Mar. 13, 2014, retrieved from https://web.archive.org/web/20140313215320/http://www.camero-tech.com/products.php, 1 page.
Agrafioti et al., "ECG based recognition using second order statistics", Proc. 6th Annual Communication Networks and Services Research Conference (CNSR 2008), Halifax, Nova Scotia, Canada, May 5-8, 2008, pp. 82-87.
Bimpas et al., "Development of a Three Band Radar System for Detecting Trapped Alive Humans Under Building Ruins", Progress in Electromagnetics Research, Pier 49, 2004, pp. 161-188.
Bragge et al., "High-Resolution QRS Detection Algorithm for Sparsely Sampled ECG Recordings", University of Kuopio, Department of Applied Physics Report Series, ISSN 0788-4672, Aug. 31, 2004, 8 pages.
Chen, Kun-Mu et al., "Microwave Life-Detection Systems for Searching Human Subjects Under Earthquake Rubble or Behind Barrier", IEEE Transactions on Biomedical Engineering, Jan. 2000, vol. 27, No. 1, pp. 105-114.

(56) References Cited

OTHER PUBLICATIONS

Chen et al., "An X-Band Microwave Life-Detection System", IEEE Transactions on Biomedical Engineering, vol. BME-33, No. 7, Jul. 1986, pp. 697-701.
Chen et al., "Measurement of Heart and Breathing Signals of Human Subjects Through Barriers with Microwave Life-Detection Systems", Proceedings of the Annual International Conference of the IEEE Engineering in Medicine and Biology Society, Nov. 4-7, 1988, pp. 1279-1280.
Chongyu et al., "The design of cancellation unit against radiofrequency interference in life-detection Radar", International Conference on Microwave and Millimeter Wave Technology, May 8-11, 2010, pp. 1758-1761.
Chuang et al., "Automatic Clutter-Canceler for Microwave Life-Detection Systems", IEEE Transactions on Instrumentation and Measurement, vol. 40, No. 4, Aug. 1991, pp. 747-750.
Chuang et al., "Microprocessor-Controlled Automatic Clutter-Cancellation Circuits for Microwave Systems to Sense Physiological Movements Remotely Through Rubble", 7th IEEE Conference on Instrumentation and Measurement Technology, Feb. 13-15, 1990, pp. 177-181.
De Pasquale et al., "RCS of human being physiological movements in the 1-10GHz bandwidth: Theory, simulation and measurements", 2008 IEEE Radar Conference, May 26-30, 2008, pp. 1-6.
Donelli, M., "A Rescue Radar System for the Detection of Victims Trapped Under Rubble Based on the Independent Component Analysis Algorithm", Progress in Electromagnetics Research M, vol. 19, Jul. 29, 2011, pp. 173-181.
Geisheimer et al., "A Non-Contact Lie Detector using Radar Vital Signs Monitor (RVSM) Technology", IEEE Aerospace and Electronic Systems Magazine, vol. 16, Issue 8, Aug. 2001, pp. 10-14.
Geisheimer et al., "Applications of Neural Networks to the Radarcardiogram (RCG)", Proc. SPIE 3722, Applications and Science of Computational Intelligence II, Mar. 22, 1999, pp. 368-377, doi:10.1117/12.342891.
Hejjel et al., "What is the adequate sampling interval of the ECG signal for heart rate variability analysis in the time domain", Physiological Measurement, vol. 25, No. 6, Sep. 14, 2004, pp. 1-7.
Hirsch et al., "Respiratory sinus arrhythmia in humans: how breathing pattern modulates heart rate", American Journal of Physiology—Heart and Circulatory Physiology, vol. 241, No. 4, Oct. 1, 1981, pp. H620-H629.
Hogenauer, "An economical class of digital filters for decimation and interpolation", IEEE Transactions on Acoustics, Speech, and Signal Processing, vol. 29, Issue 2, Apr. 1981, pp. 155-162.
Ivashov et al., "Detection of Human Breathing and Heartbeat by Remote Radar", Progress in Electromagnetic Research Symposium, Mar. 28-31, 2004, pp. 663-666.
Izadi et al., "Design and Simulation of a Life Detection System Based on Detection of the Heart Beat Using Doppler Frequency", 2006 IEEE International Symposium on Signal Processing and Information Technology, Aug. 27-30, 2006, pp. 685-690.
Jianqi et al., "A New Method for Identifying the Life Parameters via Radar", EURASIP Journal on Advances in Signal Processing, vol. 2007, Article ID 31415, Jan. 30, 2007, 8 pages, doi:10.1155/2007/31415.
Kim et al., "Segmental Hidden Markov Models with Random Effects for Waveform Modeling", Journal of Machine Learning Research 1, Oct. 2006, 27 pages.
Kong et al., "Life Detection Algorithm for Stepped-Frequency CW Radar", 2009 IET International Radar Conference, Apr. 20-22, 2009, pp. 1-4.
Li et al., "Efficient mixed-spectrum estimation with application to target feature extraction", IEEE Transactions on Signal Processing, vol. 44, Issue 2, Feb. 1996, pp. 281-295.
Lien et al., "Investigation of the LO Phase-Noise Effect and RF System Simulation for a 60-GHz Wireless Non-Contact Human Vital-Signal Detection System", 2009 4th International Symposium on Wireless Pervasive Computing, Feb. 11-13, 2009, pp. 1-4.
Liu, Zijian, "The Application of the Hilbert-Huang Transform in Through-wall Life Detection with UWB Impulse Radar", PIERS Online, vol. 6, No. 7, 2010, pp. 695-699.
Liu et al., "Feature extraction of SAR targets consisting of trihedral and dihedral corner reflectors", IEE Proc.-Radar, Sonar Navig., Jun. 1998, vol. 145, No. 3, pp. 161-172.
Lu et al., "Contact-free Measurement of Heart Rate Variability via a Microwave Sensor", Sensors, vol. 9, Issue 12, Nov. 30, 2009, pp. 9572-9581, doi:10.3390/s91209572.
Lubecke et al., "Localization of Nodes and personnel in a Multistatic Radar Sensor Network", Radar Sensor Technology XI, Proc. SPIE vol. 6547, Radar Sensor Technology XI, May 3, 2007, pp. 65470G-1-65470G-9, doi:10.1117/12.721553.
Lubecke et al., "Through-the-Wall Radar Life Detection and Monitoring", 2007 IEEE/MTT-S International Microwave Symposium, Jun. 3-8, 2007, pp. 769-772.
Morgan et al., "Novel signal processing techniques for Doppler radar cardiopulmonary sensing", Signal Processing, vol. 89, Issue 1, Jan. 2009, pp. 45-66.
Obeid et al., "Doppler radar for heartbeat rate and heart rate variability extraction", Proc. 3rd International Conference on E-Health and Bioengineering (EHIB 2011), la$i, Romania, Nov. 24-26, 2011, pp. 1-4.
Odinaka et al., "ECG biometric recognition: a comparative analysis", IEEE Trans. Inf. Forensics Security, vol. 7, No. 6, Dec. 2012, pp. 1812-1824.
Osowski et al., "Support Vector Machine-Based Expert System for Reliable Heartbeat Recognition", IEEE Transactions on Biomedical Engineering, vol. 51, No. 4, Apr. 2004, pp. 582-589.
Petrochilos et al., "Blind separation of Human Heartbeats and Respiration by the use of a Doppler Radar Remote Sensing", 2007 IEEE International Conference on Acoustics, Speech and Signal Processing—ICASSP '07, Apr. 15-20, 2007, pp. 1-333 -1-336.
Pieraccini et al., "Detection of Breathing and Heartbeat through Snow using a Microwave Transceiver", IEEE Geoscience and Remote Sensing Letters, vol. 5, No. 1, Jan. 2008, pp. 57-59.
Pizzuti et al., "Digital sampling rate and ECG analysis", Journal of Biomedical Engineering, vol. 7, Issue 3, Jul. 1985, pp. 247-250.
Plataniotis et al., "ECG biometric recognition without fiducial detection", 2006 Biometrics Symposium: Special Session on Research at the Biometric Consortium Conference, Aug. 21-Sep. 19, 2006, pp. 1-6.
Samardzjia et al., "Applications of MIMO Techniques to Sensing of Cardiopulmonary Activity", IEEE/ACES International Conference on Wireless Communications and Applied Computational Electromagnetics, Apr. 3-7, 2005, pp. 618-621.
Samardzjia et al., "Experimental Evaluation of Multiple Antenna Techniques for Remote Sensing of Physiological Motion", 2007 IEEE/MTT-S International Microwave Symposium, Jun. 3-8, 2007, pp. 1735-1738.
Scalise, Lorenzo, "Non Contact Heart Monitoring", Advances in Electrocardiograms—Methods and Analysis, InTech, Chapter 4, Jan. 2012, pp. 81-106.
Wang et al., "Analysis of human electrocardiogram for biometric recognition", EURASIP Journal on Advances in Signal Processing, vol. 2008, Article ID 148658, Sep. 19, 2007, pp. 1-11.
Wu et al., "Using the Phase Change of a Reflected Microwave to Detect a Human Subject Behind a Barrier", IEEE Transactions on Biomedical Engineering, vol. 55, No. 1, Jan. 2008, pp. 267-272.
Xu et al., "A Novel Method for Automatic Detection of Trapped Victims by Ultrawideband Radar", IEEE Transactions on Geoscience and Remote Sensing, vol. 50, Issue 8, Aug 2012, pp. 3132-3142.
Yan et al., "Life Detection Based on Cross-Correlation Analysis", 2011 IEEE CIE International Conference on Radar, vol. 2, Oct. 24-27, 2011, pp. 1356-1348
Zade et al., "A Modern Microwave Life Detection System for Human Being Buried Under Rubble", International Journal of Advanced Engineering Research and Studies, E-ISSN2249—8974, vol. 1, Issue 1, Oct.-Dec. 2011, pp. 69-77.

(56) References Cited

OTHER PUBLICATIONS

Zhou et al., "Detection of Multiple Heartbeats using Doppler Radar", 2006 IEEE International Conference on Acoustics Speech and Signal Processing Proceedings, May 14-19, 2006, pp. II-1160-II-1163.

* cited by examiner

HERMA—HEARTBEAT MICROWAVE AUTHENTICATION

CROSS-REFERENCE TO RELATED APPLICATIONS

The current application claims priority to U.S. Provisional Patent Application No. 62/038,128 filed Aug. 15, 2014, the disclosure of which is incorporated herein by reference.

STATEMENT REGARDING FEDERALLY SPONSORED RESEARCH

The invention described herein was made in the performance of work under a NASA contract, and is subject to the provisions of Public Law 96-517 (35 USC 202) in which the Contractor has elected to retain title.

FIELD OF THE INVENTION

The present invention generally relates to radars and more specifically to microwave radar sensor modules for systems and methods for detecting biometrics.

BACKGROUND

Biometrics refer to the quantifiable data (or metrics) related to human characteristics and traits. The quantifiable metrics can be gathered using various sensors and the collected data processed to identify and/or authenticate individual persons. Typically, biometric identifiers can be categorized as physiological and/or behavioral characteristics. Generally, physiological characteristics are related to the shape of the body and can include (but not limited to) fingerprint, palm print, DNA, and scent. In contrast, behavioral characteristics relate to a pattern of behavior and include (but not limited to) gait, voice, and typing rhythm. Biometric identifiers can also include characteristics that are more subtle such as respiratory and heartbeat patterns.

SUMMARY OF THE INVENTION

Systems and methods for identifying and/or authenticating individuals utilizing microwave sensing modules in accordance with embodiments of the invention are disclosed. In one embodiment, a microwave sensor module for authenticating a person using data related to the person's heartbeat includes at least one receiver configured to receive a reflected microwave signal from a person that contains information related to the person's heartbeat, a processor, a memory containing an authentication application, wherein the authentication application configures the processor to: extract heartbeat data from the reflected signal related to displacement as a result of the person's heartbeat, compare the extracted heartbeat data against at least one template profile, and authenticate the person based upon the comparison of the extracted heartbeat data and the at least one template profile.

In a further embodiment, the microwave sensor module further includes at least one transmitter configured to transmit a continuous wave (CW) radio frequency (RF) signal.

In another embodiment, the at least one transmitter is built in to a mobile device.

In a still further embodiment, the at least one transmitter is built in to an external illumination source.

In still another embodiment, the transmitted RF signal is a Bluetooth signal.

In a yet further embodiment, the transmitted RF signal is a WI-FI signal.

In yet another embodiment, the transmitted RF signal is a cellular phone signal.

In a further embodiment again, the authentication application further configures the processor to receive a portion of the transmitted RF signal using the at least one receiver, wherein the received portion of the transmitted RF signal is utilized as a reference for coherent detection.

In another embodiment again, the authentication application further configures the processor to receive a portion of the transmitted RF signal using the at least one receiver, wherein the received portion of the transmitted RF signal is utilized for noise cancellation.

In a further additional embodiment, the authentication application further configures the processor to extract heartbeat data from the reflected signal by: extracting raw data from the reflected signal by constructing an I/Q radar returns matrix and I/Q time series waveforms, bandpass filtering the I/Q time series waveforms to remove effects due to respiration and to isolate heartbeat only I/Q time series waveforms, translating and rotating the heartbeat only I/Q time series waveforms to lie along the Q-axis, where a scaled imaginary part yields heartbeat displacement waveforms, segmenting the heartbeat displacement waveforms into non-overlapping data windows (DW) of a fixed duration, and removing anomalous DW from the data set, where anomalous DW include any DW whose root mean square or maximum absolute value is outside of a specified interval.

In another additional embodiment, wherein the authentication application further configures the processor to extract heartbeat data from the reflected signal by: smoothing the I/Q time series waveforms to mitigate against outlier data points caused by motion artifacts, removing affine trends from the I/Q time series waveforms to mitigate against stationary clutter effects, and removing affine trends from the heartbeat only I/Q time series waveforms to remove residual clutter effects.

In a still yet further embodiment, a smoothed differentiator pre-filter is utilized to enhance the heartbeat data.

In still yet another embodiment, a method of authenticating a person using data related to the person's heartbeat, the method includes receiving a reflected microwave signal from a person using at least one receiver, where the reflected signal contains information related to the person's heartbeat, extracting heartbeat data from the reflected signal, where the heartbeat data is related to displacement as a result of the person's heartbeat, comparing the extracted heartbeat data against at least one template profile, and authenticating the person based upon the comparison of the extracted heartbeat data and the at least one template profile.

In a still further embodiment again, the method further includes transmitting a CW RF signal using at least one transmitter.

In still another embodiment again, the at least one transmitter is built in to a mobile device.

In a still further additional embodiment, the at least one transmitter is built in to an external illumination source.

In still another additional embodiment, the transmitted RF signal is a Bluetooth signal.

In a yet further embodiment again, the transmitted RF signal is a WI-FI signal.

In yet another embodiment again, the transmitted RF signal is a cellular phone signal.

In a yet further additional embodiment, the method further includes receiving a portion of the transmitted RF signal using the at least one receiver, wherein the received portion of the transmitted RF signal is utilized as a reference for coherent detection.

In yet another additional embodiment, the method further includes receiving a portion of the transmitted RF signal using the at least one receiver, wherein the received portion of the transmitted RF signal is utilized for noise cancellation.

In a further additional embodiment again, the extracting heartbeat data from the reflected signal includes extracting raw data from the reflected signal by constructing an I/Q radar returns matrix and I/Q time series waveforms, bandpass filtering the I/Q time series waveforms to remove effects due to respiration and to isolate heartbeat only I/Q time series waveforms, translating and rotating the heartbeat only I/Q time series waveforms to lie along the Q-axis, where a scaled imaginary part yields heartbeat displacement waveforms, segmenting the heartbeat displacement waveforms into non-overlapping data windows (DW) of a fixed duration, and removing anomalous DW from the data set, where anomalous DW include any DW whose root mean square or maximum absolute value is outside of a specified interval.

In another additional embodiment again, the extracting heartbeat data from the reflected signal further includes smoothing the I/Q time series waveforms to mitigate against outlier data points caused by motion artifacts, removing affine trends from the I/Q time series waveforms to mitigate against stationary clutter effects, and removing affine trends from the heartbeat only I/Q time series waveforms to remove residual clutter effects.

In a still yet further embodiment again, a smoothed differentiator pre-filter is utilized to enhance the heartbeat data.

DETAILED DESCRIPTION OF THE DRAWINGS

Figure 1:
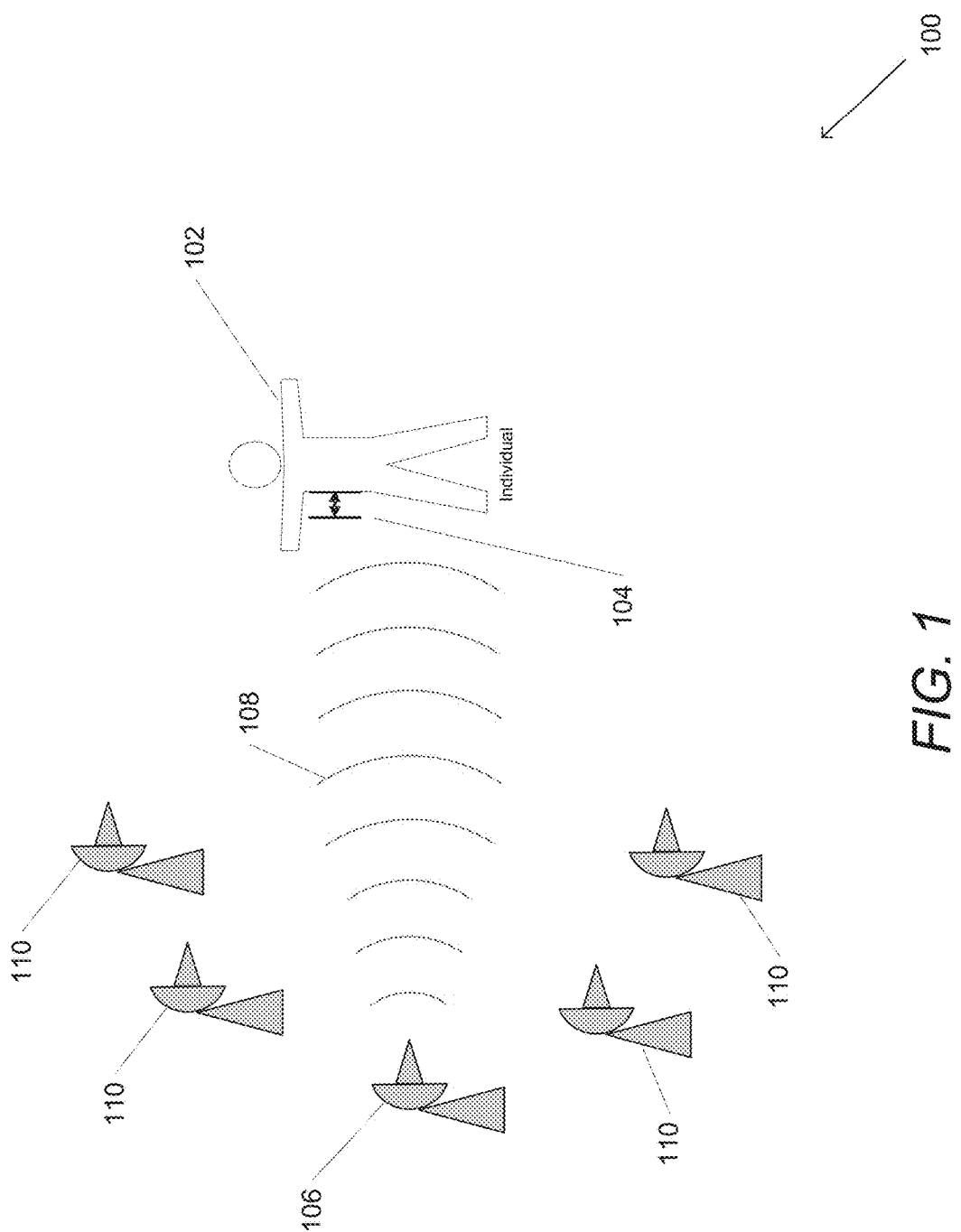
FIG. 1 is a diagram illustrating the conceptual operation of a Heartbeat Microwave Authentication (HERMA) system in accordance with an embodiment of the invention.

Turning now to the drawings, systems and methods for identifying and/or authenticating individuals utilizing microwave sensing modules in accordance with embodiments of the invention are disclosed. In many embodiments, the HEaRtbeat Microwave Authentication (HERMA) system can enable the active identification and/or authentication of a user by analyzing reflected RF signals that contain a person's unique characteristics related to their heartbeats. In various embodiments, an illumination signal is transmitted towards a person where a reflected signal captures the motion of the skin and tissue (i.e. displacement) due to the person's heartbeats. Typically, heartbeat displacement is affected by the arrangement and size of the blood vessels under the skin and thus the displacement is unique to the individual.

In many embodiments, the HERMA system utilizes a RF energy source to illuminate a person and at least one antenna to receive the reflected signal. In various embodiments, the HERMA system utilizes existing transmitters in a mobile device (e.g. Wi-Fi, Bluetooth, Cellphone signals) as the illumination source with at least one external receive antenna. As further described below, the received reflected signals can be pre-processed and analyzed to identify and/or authenticate a user. In several embodiments, a reference copy of the transmitted signal can also be used for coherent detection and noise cancellation. Although specific configurations are discussed throughout, one of ordinary skill in the art would readily appreciate that the transmitter and receivers can be varied as appropriate to the requirements of a specification application. For example, the system can utilize dedicated transmitter(s) and dedicated receiver(s) in a mobile device. In other embodiments, external illumination sources (e.g. the cell tower, TV stations, Wi-Fi Access Points) can be utilized with the at least one receiver incorporated into a mobile device. Likewise, the system could utilize existing transmitters in a mobile device and utilize receivers in the area to receive the reflection. Similarly, the system could utilize signals radiated from a bystander's mobile device as the illumination source, and receive reflections either at the subject's phone, a bystander's phone, or some other external site. HERMA systems for identifying and/or authenticating a target in accordance with embodiments of the invention are further discussed below.

Conceptual Operation of a Heartbeat Microwave Authentication (HERMA) System

The authentication process can include measuring RF reflections including (but not limited to) microwave reflections at one or more receiver locations and a predetermined time segment such as (but not limited to) 5 seconds. For any given receiver antenna position, the measured reflected signal can be an integrated sum of the signals from all places "in view." Thus, changing the antenna position or the part of the body being illuminated can change the unique pattern that is received by a microwave receiver.

A diagram illustrating the conceptual operations of a HERMA system in accordance with an embodiment of the invention is shown in FIG. 1. Typically, the HERMA system operates with an individual that is close in proximity to the unit with a clear line-of-sight path to the receiver modules. The diagram 100 includes an individual 102 that creates a displacement 104 due to their respiration and heartbeat effects. The diagram 100 illustrates a transmitter 106 that is configured to send out a continuous wave (CW) 108 signal at a predetermined frequency such as (but not limited to) 3.15 GHz. The transmitted CW signal illuminates and causes a signal to reflect from the individual 102. In various embodiments, at least one antenna 110 receives the reflected signal, where the received signal is processed. In many embodiments, the receivers can mix the received waveforms with a transmitter reference signal to produce complex baseband (i.e., in-phase (I) and quadrature (Q)) signals as further discussed below. In various embodiments, the analog complex baseband waveform can be low-pass filtered to 10 kHz and sampled at 50 kHz, and decimated to 200 Hz. In several embodiments, the received waveforms can also be recorded for 30 seconds yielding a 6,000 sample I/Q digital signal per record. Although specific conceptual operations of a HERMA system are discussed above with respect to FIG. 1, any of a variety of modes of operation including various transmitters, receivers, and combinations of transmitter and receivers, for operating a HERMA system as appropriate to the requirements of a specific application can be utilized in accordance with embodiments of the invention. Processes for authenticating users utilizing heartbeat features in accordance with embodiments of the invention are discussed further below.

Authentication Using HERMA Systems

Although users can place their devices in different position, and thus change the nature of the detected microwave heartbeat waveform, the basic heart beat timing remains unique to that person. Thus, one of the values of utilizing a HERMA approach is that it allows users to continue to use their mobile devices in the same way or manner during authentication.

Figure 2:
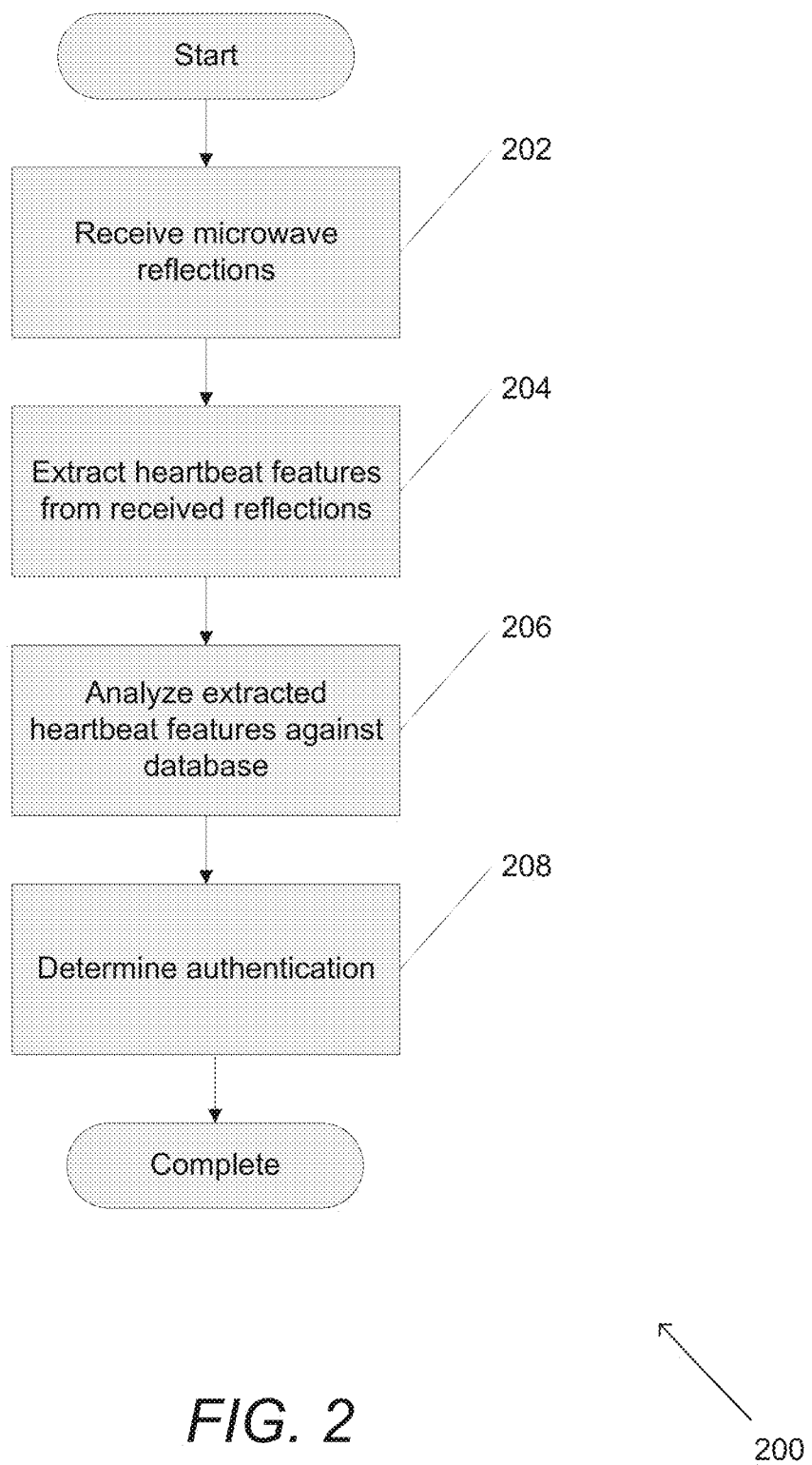
FIG. 2 is a flowchart describing a process for authenticating a user utilizing heartbeat features in accordance with an embodiment of the invention.

A process for authenticating a user utilizing heartbeat features in accordance with an embodiment of the invention is illustrated in FIG. 2. The process 200 includes receiving (202) microwave reflections from an individual at one or more receiver locations for a set period of time including (but not limited to) a 5 second segment. In many embodiments, the segment length should be long enough to capture a plurality of heartbeats. In various embodiments, the reflection data can be evaluated for corruption from interference and/or motion artifacts. The process also includes extracting (204) features related to heartbeat displacement from the received reflection signal as further discussed below. The process can further include analyzing (206) the extracted features and comparing it against a database that can include templates previously recorded of the individual being authenticated. Based on the results, a determination (208) can be made authenticating the individual as the person in question.

Figure 3:
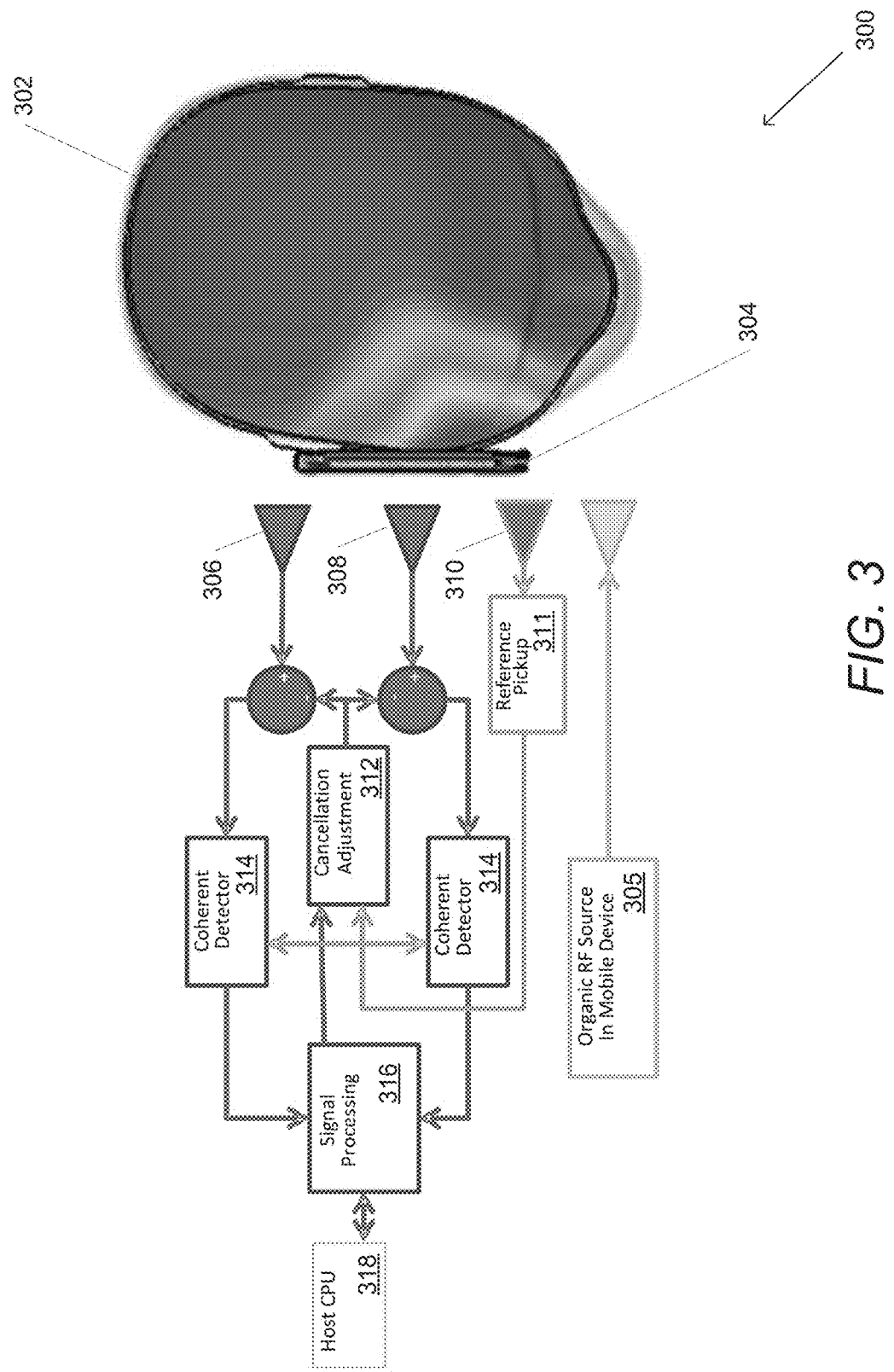
FIG. 3 illustrates a hardware design implementation of a HERMA system in accordance with an embodiment of the invention.

The process of authentication a user with HERMA can be implemented using a variety of hardware configurations. A hardware design implementation of a HERMA system in accordance with an embodiment of the invention is illustrated in FIG. 3. The diagram 300 illustrates a person 302 with a mobile device 304 that is placed near the person's right temple area. In the illustrated embodiment, the mobile device 304 is acting as an illumination source 305 of the CW transmitter signal. Typically, a mobile device may include multiple potential RF sources including (but not limited to) Bluetooth, 802.11 Wi-Fi, as well as the cellular voice and data services signals. In many embodiments, multiple receiving antennas can be utilized, where one antenna 310 can be placed close to the transmitter to pick up the reference signal 311, and the others 306, 308 can be placed farther away, so they receive a combination of the transmitted signal and the signals reflected from the subject. Typically, all antennas will receive some reflections, but the pickup antenna 310 will receive a much stronger transmit signal. As further discussed below, the reference antenna 310 does not need to be very far apart from the other antennas 306, 308 so long as the relative levels of the direct and reflected paths are different. However, each mobile device will likely have a unique optimum location for the reference antenna 310 and biometric sensing antennas 306, 308.

In several embodiments, a cancellation process can be utilized to remove a portion of the coupled signal that is not changing, and thus leaving just the variable signal from the reflections of the person. A sample of the reference signal can be used to provide a cancellation signal for cancellation adjustment 312 and as a reference for the coherent detectors 314. Cancellation adjustments utilizing various cancellation paths are disclosed in U.S. patent application Ser. No. 14/256,748, entitled "Life Detecting Radars," filed Apr. 18, 2014, the disclosure of which is incorporated by reference herein in its entirety. Using the transmitted signal as a reference allows for a narrow bandwidth detection system, reducing the amount of noise, and providing immunity to interference. In various embodiments, the HERMA system also includes a signal processing unit 316 that can be connected to a host CPU 318 or the Internet for remote access to data and control functionalities. In various embodiments, the detected signals can be digitized and processed by an application running on the host mobile device. In some embodiments, an application running on the host computer can be made aware of when the mobile device is transmitting the CW signal, or, at least, ensure that the interface is transmitting with enough to provide the needed illumination signal.

Figure 4:
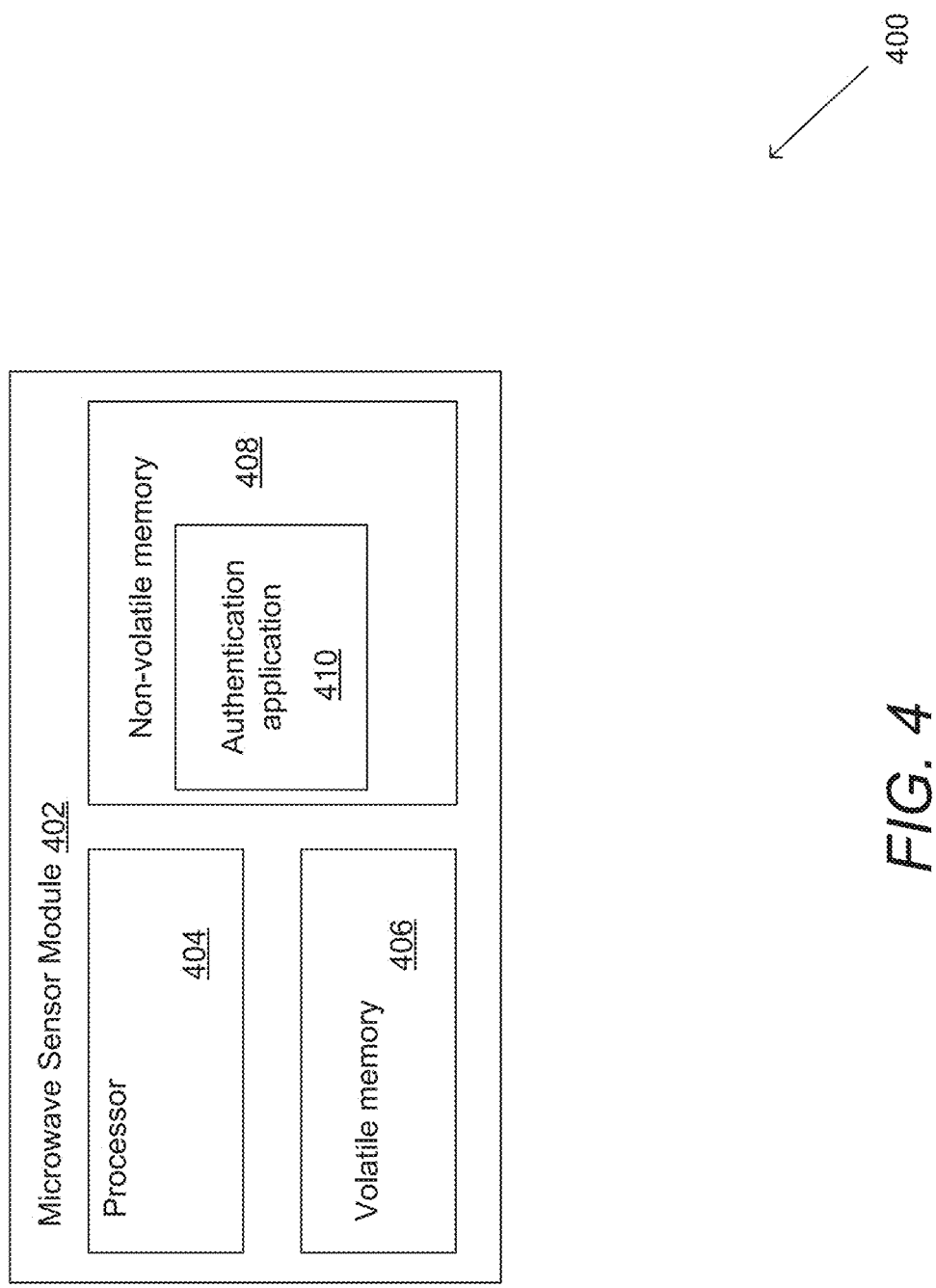
FIG. 4 is a microwave sensor module in accordance with an embodiment of the invention.

Modern cellphone and mobile device technology provides a fairly low risk path to implementation of extra circuitry needed for the sensing of the reflected microwave signals from the user. In the near term, an effective strategy may be to include the circuitry and antennas in a case that fits around the mobile device. However, the HERMA system can be implemented using hardware present on a mobile device, as a standalone module, or in combination. A microwave sensor module in accordance with an embodiment of the invention is illustrated in FIG. 4. The illustration 400 shows a sensor module 402 that includes a processor 404, volatile memory 406 and non-volatile memory. In the illustrated embodiment, the non-volatile memory 408 is a machine readable media that is utilized to store the machine readable instructions that configure the processor 404. The non-volatile memory 408 contains an authentication application 410, which is utilized to configure the processor 404 to authenticate a user utilizing heartbeat features as discussed above.

Although specific processes and hardware implementations for authenticating a user utilizing heartbeat features are discussed above with respect to FIGS. 2-4, any of a variety of processes and hardware implementations as appropriate to the requirements of a specific application can be utilized in accordance with embodiments of the invention. Processing data from a reflected signal containing displacement information (i.e. HERMA data) in accordance with embodiments of the invention are discussed further below.

Pre-Processing of HERMA Data

Electrocardiogram (ECG) based recognition generally falls into two categories: fiducial and non-fiducial methods. Fiducial methods rely on extracting timing, duration, and amplitude of features specific to ECG signal shapes. In contrast, non-fiducial methods extract features from ECG waveforms based solely on the assumption that they are unique between individuals and consistent for a given individual. As heartbeat displacements obtained from HERMA do not empirically resemble ECG signal shapes, non-fiducial methods are utilized for authentication and/or identification.

In order to apply such techniques for HERMA based systems, reflection data can be pre-processed for extraction of heartbeat displacement of an individual. Typically, the received radar returns from HERMA contain respiration and noise effects in addition to heartbeat features where respiration chest displacements are on the order of 4-12 mm at a rate of 0.1-0.3 Hz and heartbeat chest displacements are on the order of 0.2-0.5 mm at a rate of 1-3 Hz. While respiration effects are spectrally isolated from heartbeat effects, they are between 1-2 orders of magnitude larger. Because of this, harmonics from respiration may leak into the desired band of interest for heartbeat signature features (1-40 Hz). Further, the observed $1/f^2$ noise appears to adversely affect the signal-to-noise ratio (SNR) of the received heartbeat waveform noticeably.

Ideally, I/Q radar returns should trace out a circular arc in the I/Q plane centered at the origin where $x[n]=x_I+jx_Q[n]$. Further, the displacement effects $d[n]$ is equal to the displacement due to respiration $d_R[n]$ and the displacement due to heartbeat $d_H[r]$. From the I/Q radar returns, the composite displacement $d[n]$ (due to respiration $d_R[n]$ and heartbeat $d_H[n]$ effects) can be obtained as follows, where c is the speed of light and $F_0$ is the carrier frequency:

$$d[n] = \frac{c}{4\pi F_0}\arctan\left(\frac{x_Q[n]}{x_I[n]}\right)$$

Although the goal is to preserve the heartbeat displacement $d_H[n]$, in practice, the I/Q radar returns are corrupted by clutter/noise effects. For this case, the I/Q radar returns can be linearly detrend and then bandpass filter to the desired band of interest (1-40 Hz). This will yield a complex baseband signal y[n] that approximately spans a very small circular arc (between 4-8 degrees) corresponding solely to the heartbeat displacement $d_H[n]$. The signal y[n] can be translated and rotated to lie approximately along the Q-axis, yielding a signal z[n]. From this, the heartbeat displacement $d_H[n]$ can be approximately determined as follows (this process is called linear demodulation):

$$d_H[n] = \frac{c}{4\pi F_0}\text{Im}[z[n]]$$

Figure 5:
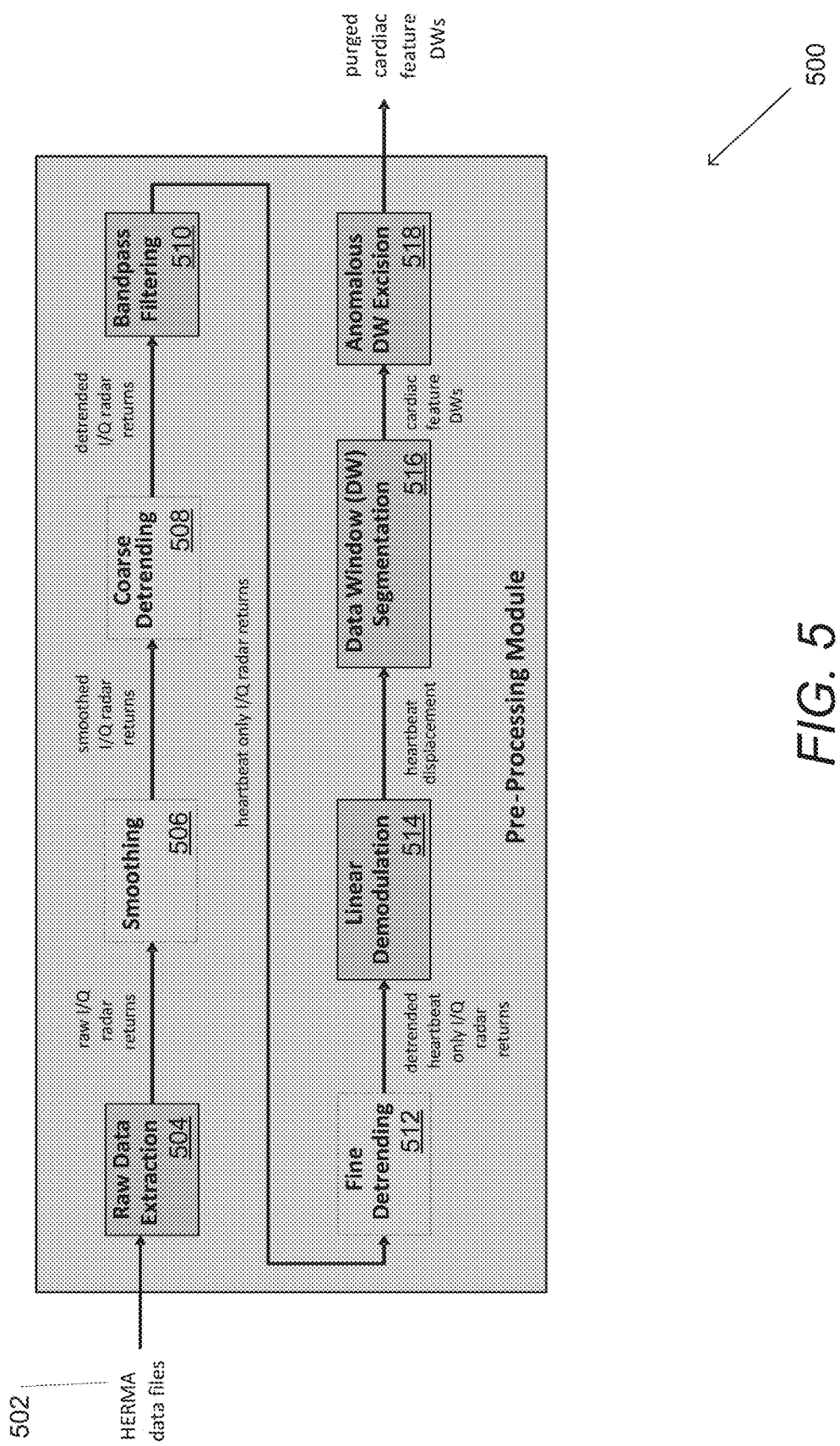
FIG. 5 is a chart illustrating a process for pre-processing reflection data in accordance with an embodiment of the invention.

A process for pre-processing reflection data in accordance with an embodiment of the invention is illustrated in FIG. 5. The process 500 includes raw data extraction (504) by reading HERMA data file(s) 502 and construction raw I/Q radar returns matrix and subject/record index matrix. An optional smoothing (506) of the I & Q time series waveforms can be carried out to mitigate against outlier data points caused by motion artifacts. The smoothing method can include a robust version of a local regression with weighted least squares and a $2^{nd}$ degree polynomial model. In some embodiments, the 'rloess' smoothing method in MATLAB was used with a window span of 1% of the total record length. Further, an optional affine (linear plus constant offset) trend can be removed (508) from the I & Q time series waveforms to mitigate against stationary clutter effects. Linearly detrending the smoothed data can help remove residual wander due to clutter. However, detrended data appears to have a prevalent respiration component. In many embodiments, time series waveforms can be bandpass filtered (510) to remove effects due to respiration and to isolate the heartbeat components. In some embodiments, a $6^{th}$ order Type II Chebyshev filter with stopband ripple of 60 dB and band edges at 0.7 Hz and 40 Hz can be used for bandpass isolation. In addition, the first 5 sec of the record can be removed to look past the bandpass filter transient effects.

An optional affine trend can also be removed (512) from the heartbeat only I & Q time series waveforms to remove residual clutter effects. In various embodiments, the input I/Q waveforms can be translated and/or rotated (i.e. linear demodulation) (514) to lie along the Q-axis and the scaled imaginary part yields the displacement. Then, each data record can be partitioned into data windows (DWs) (516) of constant size where the subject/record indices are stored. In this setting, the DWs can be formed by segmenting the heartbeat displacement waveforms into non-overlapping windows of 5 seconds in duration. To excise anomalous DWs from the data set, such as those due to motion artifacts or low signal gain, any DW whose root mean square (RMS) or maximum absolute value (MAV) is outside of a specified interval is deemed anomalous and excised (518). Consider accepting a given DW only if either the RMS or MAV of the window lied within a specified range. Large values of RMS or MAV suggest the presence of a motion transient that should be removed from the data set. Small values of RMS or MAV suggest that the gain of the signal path is too low. In this case, the heartbeat displacement waveform will look severely corrupted by noise and should be removed from the data set.

The received heartbeat displacement waveforms often possess a noticeable fundamental beat, but do not appear to have finer details as in the case of ECG signals. This may be the result of the I/Q anti-aliasing filters at the receiver modules, which noticeably shape the input noise with a $1/f^2$ type behavior. While the noise power drops off appreciably with frequency, which ensures good alias image suppression, for low frequencies, this could result in strong noise components seen in bands of interest such as the heartbeat band of 1-40 Hz. To mitigate against this effect, a smoothed differentiator pre-filter can be utilized to enhance the heartbeat fine details (i.e., the harmonics above the fundamental). This has resulted in improved authentication/identification performance for some embodiments.

Although specific processes for pre-processing reflection data are discussed above with respect to FIG. 5, any of a variety of processes for pre-processing reflection data as appropriate to the requirements of a specific application can be utilized in accordance with embodiments of the invention. HERMA implementation using 4 channel and single channel systems in accordance with embodiments of the invention are discussed further below.

4 Channel and Single Channel HERMA System Implementations

Figure 9A:
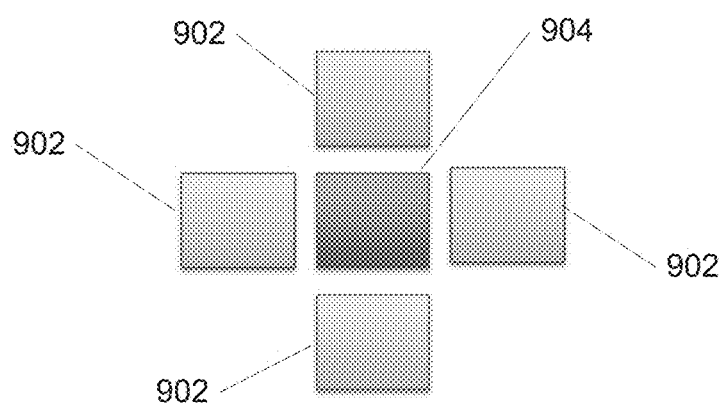
FIGS. 9A-B illustrate antenna configurations in accordance with an embodiment of the invention.

Various non-fiducial methods implicitly extracted heartbeat signature features from the normalized AC of non-overlapping constant length DWs. In these methods, the normalized AC DW sequences were mapped to feature vectors (FVs) via a data transformation. Specifically, the three methods that we looked at for HERMA were the following: (1) applying a discrete cosine transform (DCT) and using the lower frequency components to form the FVs (referred to here as the AC/DCT method); (2) applying a principal component analysis (PCA) derived from the training set to form the FVs (referred to here as the AC/PCA method) and (3) applying a PCA followed by a linear discriminant analysis (LDA) derived from the training set to form the FVs (referred to here as the AC/PCLDA method). In testing system implementations, data from HERMA was collected using two antenna configurations: (1) a 4 channel cruciform arrangement in which the transmitter antenna was placed at the center of the cruciform and (2) a single channel system in which the transmitter and receiver antennas were adjacent to each other. A 4 channel cruciform arrangement in accordance with an embodiment of the invention is shown in FIG. 9A. The arrangement 900 includes four receive antennas 902 on each side of a transmit antenna 904 that is placed in the center of the four receive antennas 902.

For the 4 channel cruciform arrangement, data was captured according to the following: 5 subjects, 3 orientations per subject (front facing, left temple profile, and right temple profile), and 2 data takes per orientation. For the single channel setup, data was captured according to the following: 6 subjects, 3 orientations per subject (front facing, left temple profile, and right temple profile), 6 data takes per orientation. For both configurations, considered both merged and separate orientations. For merged orientations, subject indices from data takes from a given individual at different orientations were merged together to correspond to one subject. For separated orientations, data takes from a given individual at different orientations were assigned separate subject indices.

The 4 channel system utilized DW construction with anomalous excision as discussed above. In particular, an experimental system used MAV criterion where only DWs with MAV levels between −80 dB and −74 dB were preserved. Thus, the original data set included 600 DWs with 5 sec non-overlapping windows from 120 record observations (5 subjects, 3 orientations, 2 takes per orientation, and 4 antenna channels per take) and the reduced data set included 163 DWs. The vast majority of the DWs that did not survive the MAV based purge came from Channels 1 & 3, which were known to yield noisy and heavily attenuated displacement signals. Further, DWs corrupted by random motion transients and artifacts were successfully removed, upon manual inspection.

Figure 6A:
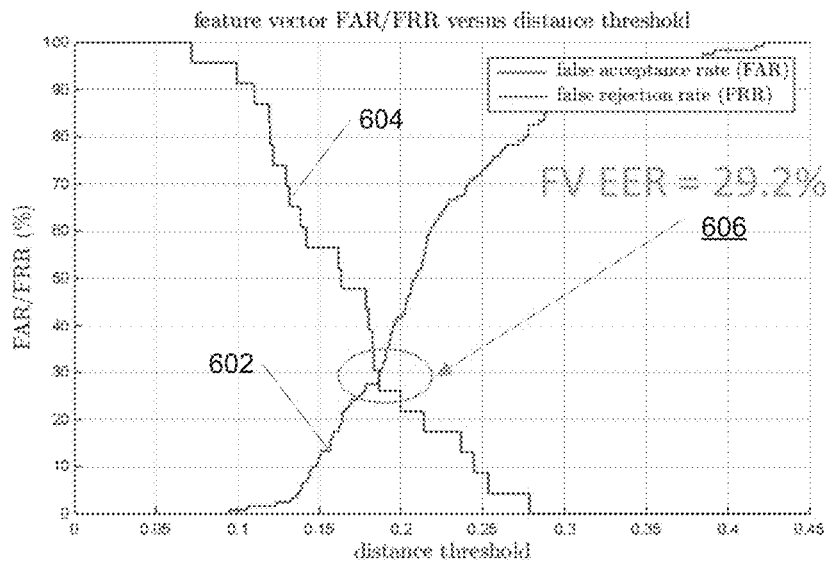
FIGS. 6A-B are graphs illustrating results from a 4 channel HERMA system with merged orientation in accordance with an embodiment of the invention.
Figure 6B:
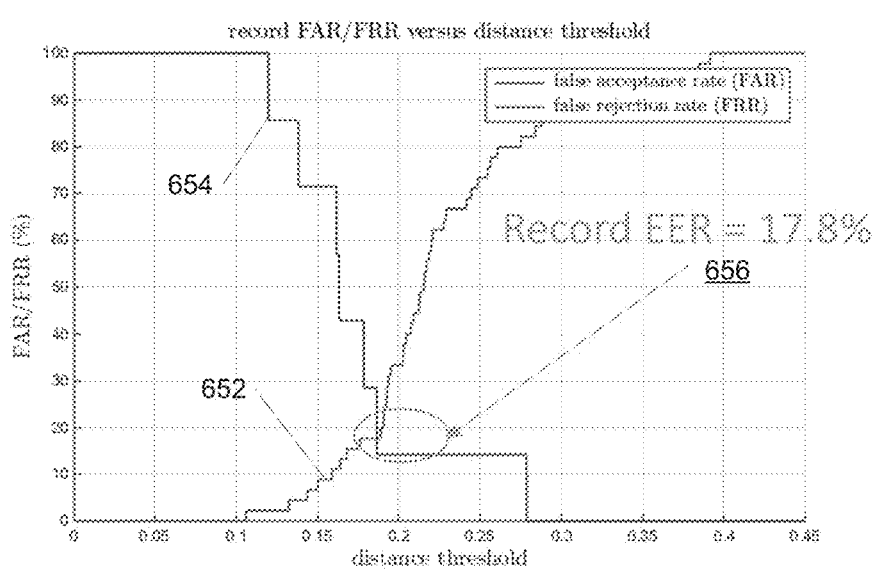

A graph illustrating results from a 4 channel system with merged orientation in accordance with an embodiment of the invention is illustrated in FIGS. 6A-B. The graph 600 of FIG. 6A depicts the false acceptance rate (FAR) 602 and the false rejection rate (FRR) 604 for a feature vector (FV) in accordance with an embodiment of the invention. The equal error rate (EER) is shown as the intersection 606 of the FAR and FRR of a value of 29%. The graph 650 of FIG. 6B depicts the FAR 652 and FRR 654 for a record vector in accordance with an embodiment of the invention. The equal error rate (EER) is shown as the intersection 656 of the FAR and FRR of a value of 17.8%. The results are also summarized below in Table 1.

Further, results as to identification using a 4 channel system with merged orientation in accordance with an embodiment of the invention are summarized below in Table 2. With anomalous DWs removed, trends were noticed with the normalized ACs between the different subjects. In various embodiments, setting the maximum lag to 1.4 seconds yielded the best results in terms of authentication and identification.

|  | # of hits | # of trials | Observed rate | Lower limit of 50% confidence interval | Upper limit of 50% confidence interval |
| --- | --- | --- | --- | --- | --- |
| FV accuracy | 46 | 88 | 0.5227 | 0.4811 | 0.5639 |
| Record accuracy | 20 | 33 | 0.6061 | 0.5321 | 0.6753 |

Figure 7A:
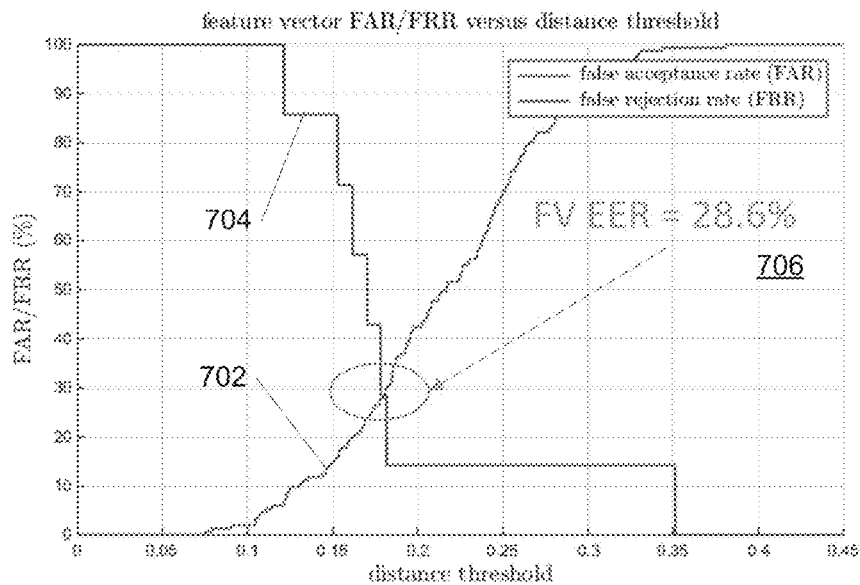
FIGS. 7A-B are graphs illustrating results from a 4 channel HERMA system with separated orientation in accordance with an embodiment of the invention.
Figure 7B:
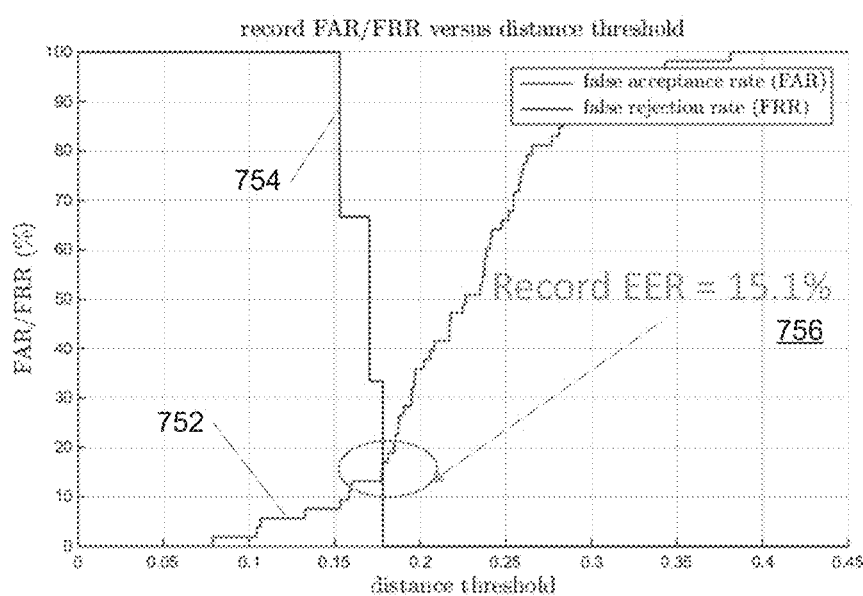

A graph illustrating results from a 4 channel system with separated orientation in accordance with an embodiment of the invention is illustrated in FIGS. 7A-B. The graph 700 of FIG. 7A depicts the FAR 702 and the FRR 704 for a feature vector in accordance with an embodiment of the invention. The EER is shown as the intersection 706 of the FAR and FRR of a value of 28.6%. The graph 750 of FIG. 7B depicts the FAR 752 and FRR 754 for a record vector in accordance with an embodiment of the invention. The EER is shown as the intersection 756 of the FAR and FRR of a value of 15.1%. The results are also summarized below in Table 3.

|  | Distance threshold value | # of hits | # of trials | Observed rate | Lower limit of 50% confidence interval | Upper limit of 50% confidence interval | Note |
| --- | --- | --- | --- | --- | --- | --- | --- |
| FV FP | 0.1864 | 35 | 120 | 0.2917 | 0.2608 | 0.3249 | Set for EER |
| FV FN | 0.1864 | 6 | 23 | 0.2609 | 0.1870 | 0.3511 | Set for EER |
| Record FP | 0.1864 | 8 | 45 | 0.1778 | 0.1340 | 0.2325 | Set for EER |
| Record FN | 0.1864 | 1 | 7 | 0.1429 | 0.0403 | 0.3407 | Set for EER |

|  | Distance threshold value | # of hits | # of trials | Observed rate | Lower limit of 50% confidence interval | Upper limit of 50% confidence interval | Note |
| --- | --- | --- | --- | --- | --- | --- | --- |
| FV FP | 0.1805 | 43 | 151 | 0.2848 | 0.2577 | 0.3138 | Set for EER |
| FV FN | 0.1805 | 2 | 7 | 0.2857 | 0.1380 | 0.4861 | Set for EER |
| Record FP | 0.1780 | 8 | 53 | 0.1509 | 0.1136 | 0.1984 | Set for EER |
| Record FN | 0.1780 | 1 | 3 | 0.3333 | 0.0914 | 0.6736 | Set for EER |

In addition, results as to identification using a 4 channel system with separated orientation in accordance with an embodiment of the invention are summarized below in Table 4.

| | # of hits | # of trials | Observed rate | Lower limit of 50% confidence interval | Upper limit of 50% confidence interval |
|---|---|---|---|---|---|
| FV accuracy | 28 | 133 | 0.2105 | 0.1845 | 0.2396 |
| Record accuracy | 10 | 44 | 0.2273 | 0.1784 | 0.2855 |

The single channel system utilized DW construction with anomalous excision as discussed above. In particular, the single channel system employed an 11-tap smoothed differentiator feature enhancement pre-filter, as it yielded slightly improved performance. Further, it used MAV criterion where only DWs with MAV levels between −123 dB and −112 dB were preserved. The original data set included 540 DWs with 5 sec non-overlapping windows from 108 record observations (3 subjects, 3 orientations, 6 takes per orientation, and 1 antenna channel per take). However, the reduced data set included 411 DWs. The DWs were plagued by weaker heartbeat signals and higher noise levels at larger frequencies were appropriately excised, upon manual inspection. In addition, DWs corrupted by random motion transients and artifacts were successfully removed.

Figure 8A:
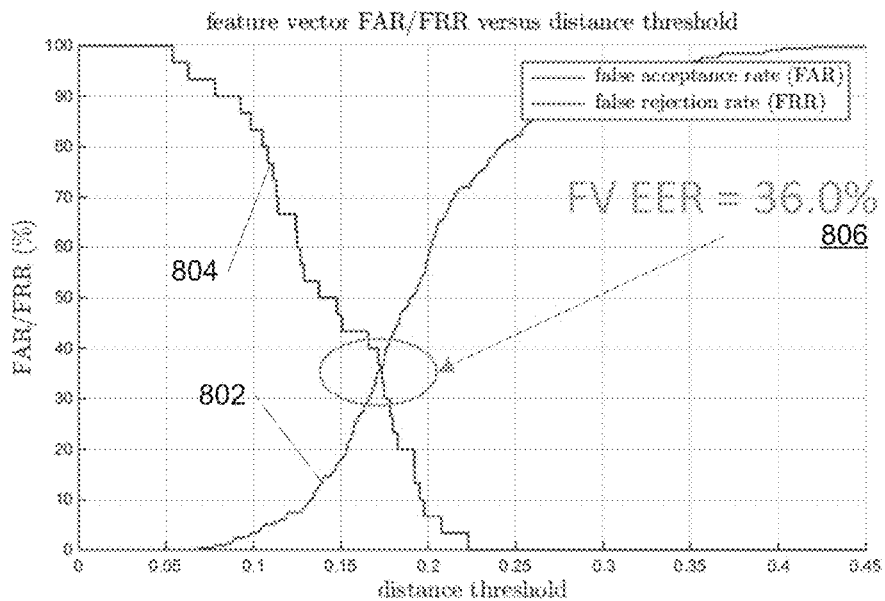
FIGS. 8A-B are graphs illustrating results from a single channel HERMA system with merged orientation in accordance with an embodiment of the invention.
Figure 8B:
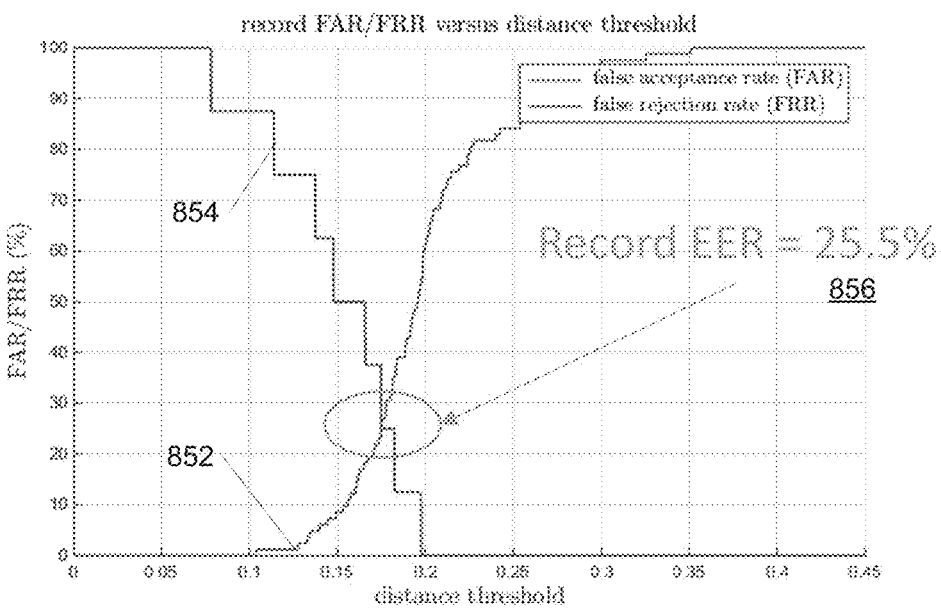

A graph illustrating results from a single channel system with merged orientation in accordance with an embodiment of the invention is illustrated in FIGS. 8A-B. The graph 800 of FIG. 8A depicts the FAR 802 and the FRR 804 for a feature vector in accordance with an embodiment of the invention. The EER is shown as the intersection 806 of the FAR and FRR of a value of 36.0%. The graph 850 of FIG. 8B depicts the FAR 852 and FRR 854 for a record vector in accordance with an embodiment of the invention. The EER is shown as the intersection 856 of the FAR and FRR of a value of 25.5%. The results are also summarized below in Table 5.

| | Distance threshold value | # of hits | # of trials | Observed rate | Lower limit of 50% confidence interval | Upper limit of 50% confidence interval | Note |
|---|---|---|---|---|---|---|---|
| FV FP | 0.1734 | 121 | 336 | 0.3601 | 0.3413 | 0.3795 | Set for EER |
| FV FN | 0.1734 | 10 | 30 | 0.3333 | 0.2638 | 0.4112 | Set for EER |
| Record FP | 0.1747 | 21 | 82 | 0.2561 | 0.2198 | 0.2967 | Set for EER |
| Record FN | 0.1747 | 2 | 8 | 0.2500 | 0.1206 | 0.4332 | Set for EER |

Further, results as to identification using a single channel system with merged orientation in accordance with an embodiment of the invention are summarized below in Table 6. With anomalous DWs removed, trends with the normalized ACs between the different subjects were noticed. In various embodiments, wetting the maximum lag to 1.3 seconds and 1.2 seconds yielded the best results in terms of authentication and identification, respectively.

| | # of hits | # of trials | Observed rate | Lower limit of 50% confidence interval | Upper limit of 50% confidence interval |
|---|---|---|---|---|---|
| FV accuracy | 38 | 156 | 0.2436 | 0.2184 | 0.2711 |
| Record accuracy | 14 | 41 | 0.3415 | 0.2828 | 0.4059 |

Although specific implementations using 4 channel and single channel HERMA systems are discussed above with respect to FIGS. 6A-9A and Tables 1-6, any of a variety of HERMA systems utilizing various transmit and receive antennas configured as appropriate to the requirements of a specific application can be utilized in accordance with embodiments of the invention.

Figure 9B:
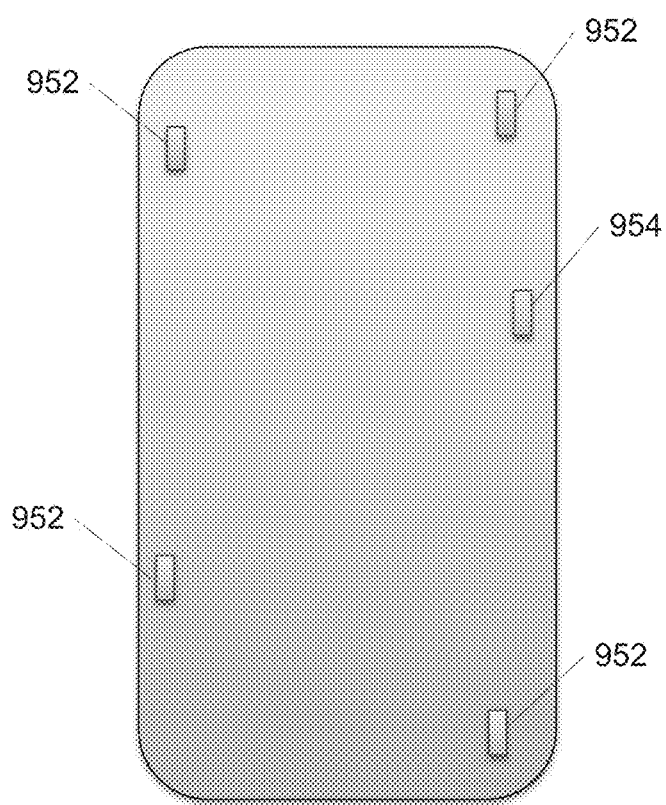

As discussed above, a HERMA system can include antennas arranged and configured as appropriate to the requirements of a specific application. For example, the antennas can be arranged and placed into a case for a particular mobile device or class of devices. An antenna configuration where the antenna positions are chosen to be close to existing antennas in a mobile device in accordance with an embodiment of the invention is illustrated in FIG. 9B. The phone case 950 includes four receive antennas 952 and a transmit antenna 954 placed where a mobile device may have various antennas including (but not limited to) main antennas, sub antennas, GPS antennas, Bluetooth and/or WLAN antennas. In various embodiments, the transmit antenna 954 can be replaced with a reference pickup antenna as described above. Although specific antenna arrangements are discussed above with respect to FIG. 9B, any of a variety of antenna arrangements for HERMA system applications as appropriate to the requirements of a specific application can be utilized in accordance with embodiments of the invention.

While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. A microwave sensor module for authenticating a person using data related to the person's heartbeat, comprising:
   at least one transmitter configured to transmit a continuous wave (CW) radio frequency (RF) signal;
   at least one receiver configured to receive a reflected microwave signal from a person that contains information related to the person's heartbeat;
   a processor;
   a memory containing an authentication application, wherein the authentication application configures the processor to:
      receive a portion of the transmitted RF signal using the at least one receiver, wherein the received portion of the transmitted RF signal is utilized as a reference for coherent detection;
      extract heartbeat data from the reflected signal related to displacement as a result of the person's heartbeat;
      compare the extracted heartbeat data against at least one template profile; and authenticate the person based upon the comparison of the extracted heartbeat data and the at least one template profile.

2. The microwave sensor module of claim 1, wherein the at least one transmitter is built in to a mobile device.

3. The microwave sensor module of claim 2, wherein the transmitted RF signal is a Bluetooth signal.

4. The microwave sensor module of claim 2, wherein the transmitted RF signal is a WI-FI signal.

5. The microwave sensor module of claim 2, wherein the transmitted RF signal is a cellular phone signal.

6. The microwave sensor module of claim 1, wherein the at least one transmitter is built in to an external illumination source.

7. The microwave sensor module of claim 1, wherein a smoothed differentiator pre-filter is utilized to enhance the heartbeat data.

8. A microwave sensor module for authenticating a person using data related to the person's heartbeat, comprising:
at least one transmitter configured to transmit a continuous wave (CW) radio frequency (RF) signal;
at least one receiver configured to receive a reflected microwave signal from a person that contains information related to the person's heartbeat;
a processor;
a memory containing an authentication application, wherein the authentication application configures the processor to:
extract heartbeat data from the reflected signal related to displacement as a result of the person's heartbeat;
compare the extracted heartbeat data against at least one template profile; and
authenticate the person based upon the comparison of the extracted heartbeat data and the at least one template profile;
wherein the authentication application further configures the processor to extract heartbeat data from the reflected signal by:
extracting raw data from the reflected signal by constructing an I/Q radar returns matrix and I/Q time series waveforms;
bandpass filtering the I/Q time series waveforms to remove effects due to respiration and to isolate heartbeat only I/Q time series waveforms;
translating and rotating the heartbeat only I/Q time series waveforms to lie along the Q-axis, where a scaled imaginary part yields heartbeat displacement waveforms;
segmenting the heartbeat displacement waveforms into non-overlapping data windows (DW) of a fixed duration; and
removing anomalous DW from the data set, where anomalous DW include any DW whose root mean square or maximum absolute value is outside of a specified interval.

9. The microwave sensor module of claim 8, wherein the authentication application further configures the processor to extract heartbeat data from the reflected signal by:
smoothing the I/Q time series waveforms to mitigate against outlier data points caused by motion artifacts;
removing affine trends from the I/Q time series waveforms to mitigate against stationary clutter effects; and
removing affine trends from the heartbeat only I/Q time series waveforms to remove residual clutter effects.

10. A method of authenticating a person using data related to the person's heartbeat, the method comprising:
transmitting a continuous wave (CW) radio frequency (RF) signal using at least one transmitter;
receiving a portion of the transmitted RF signal using at least one receiver, wherein the received portion of the transmitted RF signal is utilized as a reference for coherent detection;
receiving a reflected microwave signal from a person using the at least one receiver, where the reflected signal contains information related to the person's heartbeat;
extracting heartbeat data from the reflected signal, where the heartbeat data is related to displacement as a result of the person's heartbeat;
comparing the extracted heartbeat data against at least one template profile; and
authenticating the person based upon the comparison of the extracted heartbeat data and the at least one template profile.

11. The method of claim 10, wherein the at least one transmitter is built in to a mobile device.

12. The method of claim 11, wherein the transmitted RF signal is a Bluetooth signal.

13. The method of claim 11, wherein the transmitted RF signal is a WI-FI signal.

14. The method of claim 11, wherein the transmitted RF signal is a cellular phone signal.

15. The method of claim 10, wherein the at least one transmitter is built in to an external illumination source.

16. The method of claim 10, wherein the extracting heartbeat data from the reflected signal comprises:
extracting raw data from the reflected signal by constructing an I/Q radar returns matrix and I/Q time series waveforms;
bandpass filtering the I/Q time series waveforms to remove effects due to respiration and to isolate heartbeat only I/Q time series waveforms;
translating and rotating the heartbeat only I/Q time series waveforms to lie along the Q-axis, where a scaled imaginary part yields heartbeat displacement waveforms;
segmenting the heartbeat displacement waveforms into non-overlapping data windows (DW) of a fixed duration; and
removing anomalous DW from the data set, where anomalous DW include any DW whose root mean square or maximum absolute value is outside of a specified interval.

17. The method of claim 16, wherein the extracting heartbeat data from the reflected signal further comprises:
smoothing the I/Q time series waveforms to mitigate against outlier data points caused by motion artifacts;
removing affine trends from the I/Q time series waveforms to mitigate against stationary clutter effects; and
removing affine trends from the heartbeat only I/Q time series waveforms to remove residual clutter effects.

18. The method of claim 10, wherein a smoothed differentiator pre-filter is utilized to enhance the heartbeat data.

19. A microwave sensor module for authenticating a person using data related to the person's heartbeat, comprising:
at least one transmitter configured to transmit a continuous wave (CW) radio frequency (RF) signal;
at least one receiver configured to receive a reflected microwave signal from a person that contains information related to the person's heartbeat;
a processor;

a memory containing an authentication application, wherein the authentication application configures the processor to:
    receive a portion of the transmitted RF signal using the at least one receiver, wherein the received portion of the transmitted RF signal is utilized for noise cancellation;
    extract heartbeat data from the reflected signal related to displacement as a result of the person's heartbeat;
    compare the extracted heartbeat data against at least one template profile; and
    authenticate the person based upon the comparison of the extracted heartbeat data and the at least one template profile.

20. The microwave sensor module of claim 19, wherein the at least one transmitter is built in to a mobile device.

21. The microwave sensor module of claim 19, wherein the at least one transmitter is built in to an external illumination source.

22. A method of authenticating a person using data related to the person's heartbeat, the method comprising:
    transmitting a continuous wave (CW) radio frequency (RF) signal using at least one transmitter;
    receiving a portion of the transmitted RF signal using at least one receiver, wherein the received portion of the transmitted RF signal is utilized for noise cancellation;
    receiving a reflected microwave signal from a person using the at least one receiver, where the reflected signal contains information related to the person's heartbeat;
    extracting heartbeat data from the reflected signal, where the heartbeat data is related to displacement as a result of the person's heartbeat;
    comparing the extracted heartbeat data against at least one template profile; and
    authenticating the person based upon the comparison of the extracted heartbeat data and the at least one template profile.

23. The method of claim 22, wherein the at least one transmitter is built in to a mobile device.

24. The method of claim 22, wherein the at least one transmitter is built in to an external illumination source.

\* \* \* \* \*